United States Patent [19]

Adachi

[11] 4,389,392

[45] Jun. 21, 1983

[54] DETERMINATION OF TUMOR ASSOCIATED GLYCOLINKAGE AND DIAGNOSIS OF CANCERS

[75] Inventor: Masakazu Adachi, Takasaki, Japan

[73] Assignee: Otsuka Pharmaceutical Co., Ltd., Tokyo, Japan

[21] Appl. No.: 187,890

[22] Filed: Sep. 17, 1980

Related U.S. Application Data

[63] Continuation-in-part of Ser. No. 116,727, Jan. 30, 1980, abandoned.

[30] Foreign Application Priority Data

Jan. 30, 1979 [JP] Japan .................................... 54/9435
Nov. 1, 1979 [JP] Japan .................................... 54/141741

[51] Int. Cl.³ .................... G01N 33/56; G01N 33/58; G01N 33/60
[52] U.S. Cl. .................................. 424/1; 260/112 R; 260/112 B; 422/61; 436/64
[58] Field of Search .................... 424/1, 12; 23/230 B; 260/112 B, 112 R; 422/61

[56] References Cited

U.S. PATENT DOCUMENTS

| | | | |
|---|---|---|---|
| 4,132,767 | 1/1979 | Tohmatsu et al. | 424/1 |
| 4,146,603 | 3/1979 | Davidson et al. | 424/1 |
| 4,152,410 | 5/1979 | Ishii | 424/1 |
| 4,174,385 | 11/1979 | Reid | 424/1 |
| 4,196,186 | 4/1980 | Bogoch | 424/12 |
| 4,289,747 | 9/1981 | Chu | 424/1 |
| 4,298,590 | 11/1981 | Bogoch | 424/1 |
| 4,311,686 | 1/1982 | Angers et al. | 424/1 |

OTHER PUBLICATIONS

Lotan et al., J. Biolog. Chem., vol. 250, Nov. 1975, pp. 8518-8523.
Prieels et al., Proc. Natl. Acad. Sci. USA, vol. 75, No. 5, May, 1978, pp. 2215-2219.
Pereira et al., Carbohydrate Res., vol. 51, 1976, pp. 107-118.

*Primary Examiner*—Christine M. Nucker
*Attorney, Agent, or Firm*—Sughrue, Mion, Zinn, Macpeak, and Seas

[57] ABSTRACT

A method for determining the level of tumor associated glycolinkage containing substance (TAG) in a sample of body fluid which comprises reacting the TAG in a sample of the body fluid with a lectin to form a TAG-lectin complex and measuring the amount of the TAG-lectin complex or an unreacted lectin and a kit for use in such method are disclosed. The method is useful for the diagnosis of various cancers or tumors.

26 Claims, 2 Drawing Figures

DETERMINATION OF TUMOR ASSOCIATED GLYCOLINKAGE AND DIAGNOSIS OF CANCERS

CROSS REFERENCE TO RELATED APPLICATIONS

This application is a continuation-in-part application of Ser. No. 116,727, filed Jan. 30, 1980, now abandoned.

BACKGROUND OF THE INVENTION

1. Field of the Invention

This invention relates to determination of the level of tumor associated glycolinkage containing substances, i.e., sugar related substances including glycoproteins, glycopeptides, glycolipids and sugars (hereafter TAG) in a sample of body fluids of mammals, more particularly those TAG which increase as undifferentiated cells, especially tumor or cancer cells proliferate, and diagnosis of cancer based on such determination.

2. Description of the Prior Art

It has heretofore been used a method of determining the level of specific glycoproteins in a sample of body fluids of patients with cancer. This process makes use of the antigenicity mainly of the protein moiety of the glycoproteins. For example, $\alpha_1$-foetoprotein level and carcinoembryonic antigen (hereafter CEA) level are determined for the diagnosis of primary hepatoma and of cancers of digestive organs, particularly rectal cancer, etc. (cf. *Igaku no Ayumi*, vol. 106, No. 5, Fifth Saturday Special Issue, pp. 235–250 (1978)). However, these methods are not satisfactory since their applicability is limited to certain types of cancers and tumors.

On the other hand, no diagnostic method utilizing the linking specificity of the sugar residue of TAG is known heretofore.

There is a long existing need for a simple, inexpensive quantitative methodology to determine TAG levels in body fluids which has a wide applicability.

SUMMARY OF THE INVENTION

Paying attention to the fact that in the body fluids of individuals or patients with cancer there is present TAG produced by undifferentiated cells (mostly cancer cells) and released into the body fluid and that TAG is drastically different from glycolinkage containing substances produced by differentiated cells (mostly normal cells) and released into the body fluids in the chemical structure of the sugar chain, its length and the composition of sugar residues, extensive investigations have been made which have led to the discovery that TAG has a galactose-($\beta1\rightarrow3$ or $\beta1\rightarrow4$)-N-acetylglucosamine and/or -N-acetylgalactosamine terminal(s) and binds specifically with lectins, and that the TAG level in a sample of body fluid can be determined by reacting the TAG with a lectin. The TAG level will indicate presence or absence of cancer cells, degree of proliferation thereof and rise and fall thereof and permit successful diagnosis of various cancers or tumors. This invention is based on the above discovery.

Thus, this invention provides a method for determining the TAG level in a sample of body fluid which comprises reacting the TAG in a sample of the body fluid with a lectin to form a TAG-lectin complex and measuring the amount of the TAG-lectin complex or an unreacted lectin, and a kit for use in such method.

DETAILED DESCRIPTION OF THE INVENTION

Figure 1:
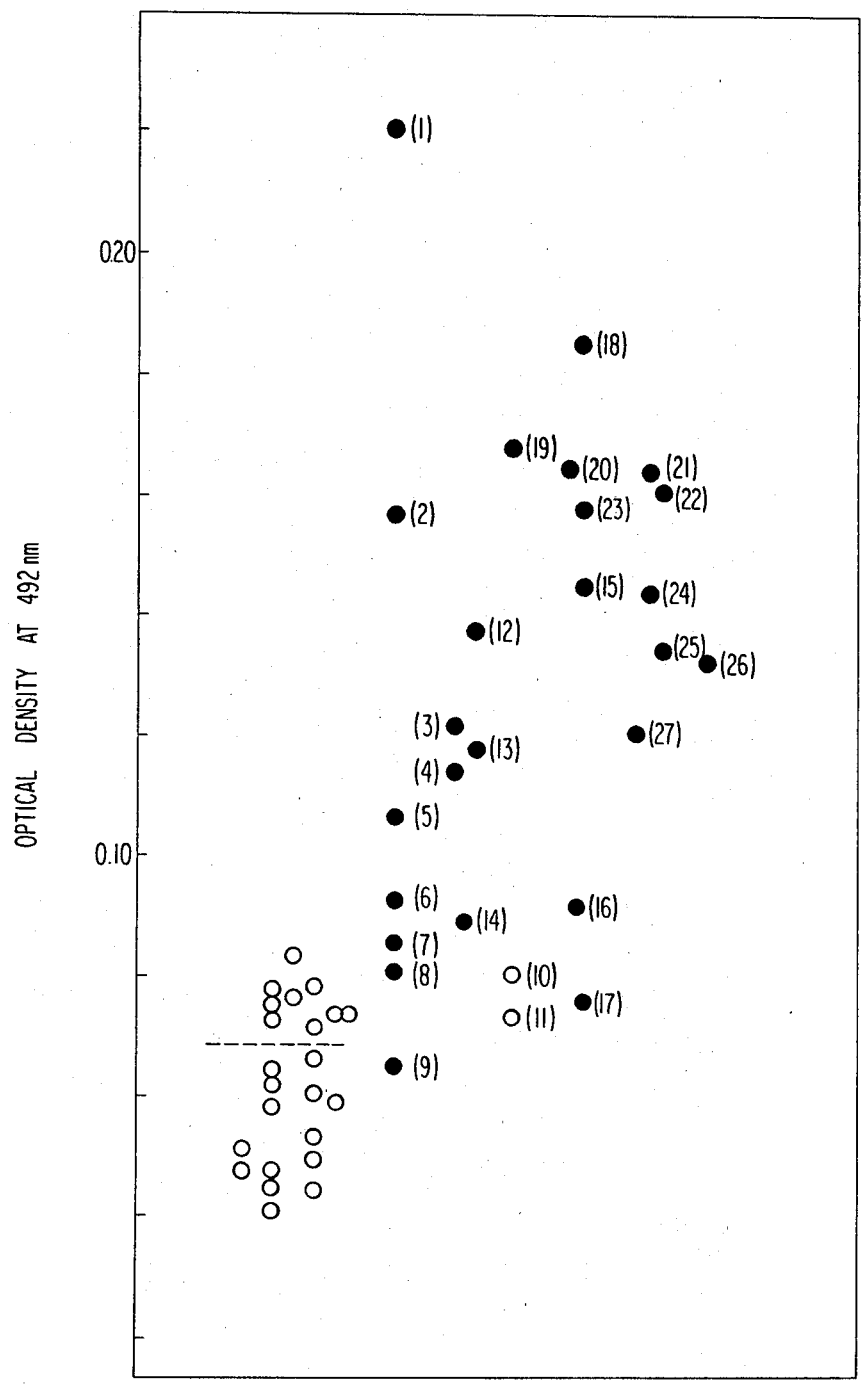
FIG. 1 is a graph representing the amounts of TAG determined in accordance with Example 1 of this invention.

Various body fluids can be used in this invention. Examples of suitable body fluids include blood, tissue fluids, lymph, hydrothorax, ascites, amniotic fluid, gastric juice, urine, pancreatic juice, cerebrospinal fluid, saliva, etc. Of these blood, especially in the form of serum or plasma is preferred.

The amount of body fluid for samples is usually about 1 to about 10 ml, preferably 2 to 5 ml.

In this invention the determination of TAG level in a sample of body fluid can be carried out either by isolating or separating TAG from the body fluid reacting it with a lectin to form a TAG-lectin complex and measuring the amount of the TAG-lectin complex or unreacted lectin after separation thereof, or by adding a labeled lectin to the body fluid sample directly to form TAG-labeled lectin complex, separating the resulting TAG-labeled lectin complex or unreacted labeled lectin and measuring the amount thereof.

To separate the TAG fraction from a body fluid sample, conventional methods for the extraction or separation of glycolinkage containing substances such as salting out, precipitation, extraction with solvents, centrifugation, dialysis, molecular sieve, enzyme inactivation, etc., or a combination of one or more of them can be used. For example, TAG fraction can be obtained by adding a precipitation or denaturation effective amount of sulfosalicylic acid, trichloroacetic acid or zinc sulfate to blood serum or plasma, or heating the blood serum or plasma to precipitate albumin, immunoglobulin and the like, removing the precipitated proteins by filtration and dialysing the filtrate.

In cases where a labeled lectin is used, the body fluids collected other than blood can be used as is as a test sample (hereafter "sample"). It is, however, preferred to add a protein having a low sugar content such as bovine serum albumin (BSA), etc. as a protective protein in order to prevent the sample from denaturing and at the same time promote the reaction with lectin. More preferably, an appropriate amount of the protective protein is added to samples after removing albumins, immunoglobulins, etc. from the samples since this permits determination under more controlled conditions. When using blood samples, blood serum obtained by the conventional blood serum collecting method, or blood plasma obtained by the conventional blood plasma collecting method using an anticoagulant such as heparin, EDTA, citric acid, etc. can be used as a sample, with blood plasma collected using heparin as an anticoagulant being preferred. Samples can be diluted with water or suitable aqueous buffer solutions, if necessary or desired, e.g., in cases where the TAG level is relatively high as in ascites, etc.

In this invention those lectins which can specifically combine with galactose-($\beta1\rightarrow3$ or $\beta1\rightarrow4$)-N-acetylglucosamine and/or -N-acetylgalactosamine as described in *J.B.C.*, 250, 8518–8523 (1975); *Biochem. Biophys. Res. Comm.* 62, 144 (1975); *Z. Immunitaetsforch,*

138, 423–433 (1969) *Br. J. Exp. Pathol.* 27, 228–236 (1946); *Proc. Nathl. Acad. Sci. USA,* 75, No. 5, 2215–2219 (1978); *Biochemistry* 13, 196–204 (1974), *Carbohydrate Research,* 51, 107–118 (1976), etc., for example, peanut lectin, castor bean (*Ricinus communis*) lectin, etc. can be used.

Substances which can be used for labeling lectins and thereby make them detectable by radiometric, fluorimetric, colorimetric and like means are enzymes, fluorescent substances and radioactive substances. Examples of suitable enzymes include glucoamylase, glucose, oxidase, peroxidase, alkaline phosphatase, $\beta$-galactosidase, hemeoctapeptide, etc. and active fragments thereof. Examples of suitable fluorescent substances include fluorescein, fluorescein isothiocyanate, rhodamin, dansyl chloride (i.e., 5-dimethylamino-1-naphthalenesulfonyl chloride), etc. Examples of suitable radioactive substances include radioactive iodine, tritium, etc. To label lectins with the above-described labeling substances, any conventional methods employed for labeling known proteins such as antigens and antibodies with enzymes, fluorescent substances and radioactive substances can be used. For example, lectins can be labeled with radioactive isotopes according to the method described in Kazuo Shizunome and Yuichi Kumahara: "Radioimmunoassay" pp. 45–56 (1978) published by Asakura Publishing Co., Tokyo.

In the method of this invention labeled or unlabeled lectins are preferably used in admixture with suitable solvents. Any solvents which do not denature labeled or unlabeled lectins, for example, physiological salt solution, water, 0.1 M tris-HCl buffer solution (pH: about 7.5), 0.1 M phosphate buffer solution (pH: about 7.4) etc. can be used. The amount of lectin contained in the solvent or diluent can be chosen depending on agglutination value (which is defined in terms of a final or maximum dilution of serially 2-fold diluted samples), the type of label, or the substances to be determined, etc. and usually is about 0.01 to about 100 $\mu$g/ml, preferably 0.03 to 40 $\mu$g/ml. The above labeled or unlabeled lectin solutions can be diluted further.

In order to practice the method of this invention, a predetermined amount of TAG fraction or body fluid per se is mixed with a given amount of lectin or labeled lectin, respectively and the resulting mixture is allowed to stand for reaction at about 45° C. or less, preferably about 4° to 40° C., most preferably about 20° to 40° C. The TAG-unlabeled or labeled-lectin complex or the unreacted unlabeled or labeled lectin, can be separated from the reaction mixture by any conventional separating technique, for example chromatography, electrophoresis, salting out, fractionation, dialysis, gel filtration, adsorption or a combination of them or a separation method using agar gel, agarose gel or polyacrylamide gel.

In greater detail, to separate the unreacted labeled or unlabeled lectin from the reaction mixture, a suitable amount of a precipitant for the TAG-lectin complex can be added to the above reaction mixture and the resulting complex can be removed, e.g., by centrifugation thereby obtaining the unreacted labeled or unlabeled lectin fraction as a supernatant. Representative precipitants are polyethylene glycol, ammonium sulfate (to saturation), Rivanol (acrinol), etc. The conditions for centrifugation can be chosen appropriately depending on the precipitants used. For example, when polyethylene glycol is used as a precipitant it is preferred to perform centrifugation at about 1,000 G for about 30 to 60 minutes.

In cases where TAG-labeled or unlabeled lectin complex is isolated from the unreacted lectin, the complex can be separated with ease from the unreacted lectin utilizing the difference in diffusion speed between the complex and unreacted lectin on agar gel, agarose gel or polyacrylamide gel. More particularly, when the reaction mixture is layed on the gel in a vessel unreacted lectin diffuses into the gel which the TAG-lectin complex remains on the gel, i.e., outside the gel without being diffused. Thus, they can be separated from each other with ease in the conventional manner. There is no limitation in the preparation of the gels and conventionally used methods can be employed for this purpose. For example, a certain amount of agar, agarose or polyacrylamide is added to a diluent which will not cause denaturation of proteins such as distilled water, citrate or Tris-HCl buffer solution (pH: about 7.5), etc. followed by heating at 60° to 80° C. with gently stirring to dissolve and the solution is poured into a suitable vessel such as a test tube and allowed to cool to congeal like jelly. The concentration of the gel is chosen depending on the dimension (e.g., molecular weight, stereostructure, etc.) of the labeling substance and TAG-labeled lectin complex. Usually gels of about 0.4 to 2.0% by weight, preferably 0.7 to 1.0% by weight are used in this invention. The resulting gel can contain a preservative if necessary or desired. The surface of the gel thus prepared may be flat or concave, with the latter form being preferred since complexes to be formed will not adhere on the wall of the vessel.

The amount of the TAG-labeled or unlabeled lectin complex or unreacted labeled or unlabeled lectin is measured by the conventional method and the TAG level in the body fluid can be calculated from the value obtained.

For measurement of the amount of the residual unlabeled lectin various methods can be used. It is preferred, however, to add to samples a substance capable of reacting with the lectin specifically to agglutinate or precipitate it and observe the change visually or by measuring using an optical analysis, e.g., optical density. Examples of suitable lectin agglutinating substances include glycoproteins having a galactose-($\beta$1→3 or $\beta$1→4)-N-acetylglucosamine terminal, for example, rabbit erythrocyte, neuraminidase treated sheep erythrocyte, etc., and Sephadex, glass beads, etc. coated with the above-described glycoproteins.

Practically, this method can be carried out as follows. The above-described reaction mixture is diluted serially with two-fold dilution with a diluent, e.g., 0.15 M phosphate buffer solution, physiological salt solution, etc., and aliquots of the dilution are placed on V- or U-form plates or slide glasses or in small test tubes or the like and each mixed with a substance capable of agglutinating the lectin specifically with stirring and the plates or the like bearing the mixture are allowed to stand at 45° C. or less, preferably 4° to 40° C. for 30 minutes or more, preferably 60 to 90 minutes to observe final or maximum dilution at which agglutination will still occur. This maximum dilution is defined as agglutination value. The lectins which can be used in this invention exhibit substantially the same agglutination value.

In cases where labeled lectins are used, the determination of TAG level can be performed by a method suited for measuring labeled substances for lectins. For example, after separating TAG-lectin complex and unreacted labeled lectin from each other the amount of TAG-labeled lectin complex or unreacted labeled lectin can be determined by selecting an appropriate substrate for an enzyme which substrate can be analyzed by colorimetric or fluorimetric analysis and determining the activity of the enzyme when the lectin is labeled therewith; by determining the intensity of fluorescence when the lectin is labeled with a fluorescent substance; or by determining the radioactivity when the lectin is labeled with a radioactive substance. For example, when an enzyme (e.g., peroxidase) is used for labeling lectin, a predetermined amount of the reaction mixture is dropped on the surface of the gel in a test tube and allowed to stand at about room temperature, preferably 4° to 25° C. for 1 to 48 hours. Then, a given amount of a suitable substrate for the enzyme (e.g., hydrogen peroxide) is added to the reaction mixture thus treated to effect enzymatic reaction followed by stopping it in an appropriate period of time and the optical density of the resulting mixture is measured if necessary using a dye or color former (e.g., o-phenylenediamine). Alternatively, when a fluorescent substance is used for labeling lectin, a predetermined amount of diluent such as a buffer solution is added to the reaction mixture on the gel after incubation and the intensity of fluorescence of the resulting mixture is measured.

A particularly convenient procedure for carrying out the method described herein is by means of a kit for the determination of TAG in a body fluid, such as plasma or serum. Such a kit can include a reagent containing a plant lectin as a specific agglutinating agent for TAG. The lectin reagent can also contain a stabilizer and/or preservative for lectin, such as proteins having a low sugar content, e.g., such as bovine serum albumin. In a preferred embodiment, this plant lectin reagent can be lyophilized and a reconstituting reagent containing an aqueous based or a water-miscible solvent (pH about 6 to 7.8, preferably 7 to 7.2) can also be included in the kit. The reagents may optionally also contain buffers for maintaining the reconstituted reagent system at a controlled pH and preservatives and/or stabilizers intended to prevent deterioration of the material prior to use. Although buffers are not considered a critical component of the kit reagents, preferably a pH of about 6 to 7.8, more preferably pH 7 to 7.2 would be used in carrying out the present method. The reconstituting reagent preferably can contain water as a solvent. For example, physiological salt solution, phosphate buffer solution, etc. can be used as a reconstituting agent. Further, a water-miscible solvent which will not affect the reaction adversely may be added.

As stated hereinabove the TAG level in a sample of body fluid can be determined advantageously in accordance with this invention. Further, this invention which permits recognition of tumor associated glycolinkage enjoys a wide applicability to various cancers or tumors as compared with conventional methods or systems utilizing antigenicity and recognizing mainly the protein moiety of glycoproteins such as CEA, $\alpha_1$-foetoprotein, etc. and is applicable to the diagnosis of any cancers or tumors such as gastric cancer, mammary cancer, colon cancer, rectal cancer, ovarian cancer, oral cavity cancer, tongue cancer, larynx cancer, prostate cancer, liposarcoma, malignant melanoma, malignant lymphoma, gastric primary sarcoma, hepatoma, etc. in their early to late stages with ease and therefore this invention is very useful for the detection of cancers in their initial stages.

This invention will be explained in greater detail with reference to Examples which should be construed as being non-limitative.

Unless otherwise indicated all parts or percentages used hereinafter are by weight.

EXAMPLE 1

Determination Using Inhibition Reaction of Blood Cell Agglutination (i) Preparation of Test Sample Blood was collected from each of 7 patients with gastric cancer, 4 patients with lung cancer, 3 patients with mammary cancer, and one patient each with colon cancer, rectal cancer, ovarian cancer, oral cavity cancer, tongue cancer, larynx cancer, uterine cancer, prostate cancer, malignant melanoma, liposarcoma, malignant lymphoma and gastric primary sarcoma as well as 7 healthy persons and plasma samples were prepared in the conventional manner. To the plasma samples was added a 6% aqueous sulfosalicylic acid solution portionwise with stirring till the proportion of the additive to the plasma became 1:1 by volume. After stirring sufficiently the mixture was centrifuged at 3,000 to 3,500 rpm for 10 minutes and the supernatant was dialyzed with water and 0.15 M phosphate buffer solution for 24 hours to prepare test sample.

(ii) Determination

To each of test samples obtained in (i) above was added an equivolume of 0.15 M phosphate buffer solution having dissolved therein 0.8 μg/ml of peanut lectin (a product of E.Y. LABORATORIES INC.) and the mixture was reacted with stirring at 20° to 37° C. for 30 minutes. The reaction mixture was diluted with a 0.15 M phosphate buffer solution to obtain a series of twofold dilutions each of which was placed on a V-form plate in an amount of 50 μl and mixed with 50 μl of rabbit erythrocyte ($1 \times 10^8$ to $2 \times 10^8$ cells/ml) with stirring. After allowing the dilution at 37° C. for 1 hour occurrence of agglutination of erythrocyte in each dilution was observed. Maximal dilution value at which the agglutination still occurred was defined as agglutination value and judgement was made using this value. The results obtained are shown in Table 1 below.

TABLE 1

| Agglutination Value | Affliction | | | | | | | | | | | | | | | |
|---|---|---|---|---|---|---|---|---|---|---|---|---|---|---|---|---|
| | I | II | III | IV | V | VI | VII | VIII | IX | X | XI | XII | XIII | XIV | XV | XVI |
| 1024 | ++ | | | | | | | | | | | | | | | |
| 512 | ++ | | | | | | | | | | | | | | | |
| 256 | | | | | | | | | | | | | | | | |
| 128 | +++ | | | | | | | | | | | | | | | |
| 64 | — | — | — | — | — | — | — | — | — | — | — | — | — | — | — | — |
| 32 | | + | | | | | | | | | | + | | | | + |
| 16 | | | | | | | | | | | | | | | | |
| 8 | | +++ | + | | | + | | | | + | | + | + | | | |
| 4 | | | + | | | + | | | | | | | | | | |
| 2 | | | | | | | | | | | | | | | | |

TABLE 1-continued

| Agglutination Value | Affliction | | | | | | | | | | | | | | | |
|---|---|---|---|---|---|---|---|---|---|---|---|---|---|---|---|---|
| | I | II | III | IV | V | VI | VII | VIII | IX | X | XI | XII | XIII | XIV | XV | XVI |
| 1 | | +++ | + | ++++ | + | | | + | + | | | + | | + | + | |

Notes:
I Healthy person
II Gastric cancer
III Mammary cancer
IV Lung cancer
V Colon cancer
VI Rectal cancer
VII Ovarian cancer
VIII Oral cavity cancer
IX Tongue cancer
X Larynx cancer
XI Uterine cancer
XII Prostate cancer
XIII Liposarcoma
XIV Malignant melanoma
XV Malignant lymphoma
XIV Gastric primary sarcoma (iii) Observation As will be clear from the results shown in Table 1 above, all the healthy persons showed agglutination value of 128 or more while patients with cancers exhibited much lower agglutination value than the healthy: Six of 7 patients with gastric cancer showed an agglutination value of 8 or lower and the rest showed that of 32. All four patients with lung cancer showed an agglutination value of 1. With respect to other cancer almost all the patients had agglutination values of 8 or less with exceptions being an agglutination value of 32 observed with one patient with uterine cancer and another with gastric primary sarcoma.

As stated above, agglutination value observed in patients with malignant tumor or cancer is always 32 or less while that of the healthy is 128 or more.

Therefore, this method provides an efficient method of determining TAG level in a sample of body fluid outside the body and can be useful in diagnosing various malignant tumors or cancers.

EXAMPLE 2

Determination Using Enzyme-Labeled Lectin

Reference Step:
(i) Activation of Peroxidase

To 1 ml of 0.3 M aqueous sodium hydrogen carbonate solution having dissolved therein 5 mg of peroxidase derived from horse raddish was added 0.1 ml of 0.1 M fluorodinitrobenzene ethanol solution and the mixture was stirred gently for 1 hour at room temperature. Then, 1 ml of 0.06 M aqueous $NaIO_4$ solution was added to the mixture which was stirred gently at room temperature for 30 minutes. The resulting mixture was further mixed with 1 ml of 0.1 M aqueous ethylene glycol solution and stirred gently at room temperature for 1 hour followed by dialysing the reaction mixture with 0.01 M carbonic acid-sodium hydrogen carbonate buffer solution (pH 9.5) at 4° C. for a day to obtain activated peroxidase preparation.

(ii) Labeling of Lectin with Peroxidase

Five mg of lectin (peanut lectin) was dissolved in 3 ml of the peroxidase preparation obtained in (i) above and the mixture was stirred gently at room temperature for 2 to 3 hours for reaction. After adding 5 mg of $NaBH_4$ thereto the reaction mixture was allowed to stand at 4° C. for 3 hours and the resulting solution was dialysed with 0.1 M Tris-HCl buffer solution (pH 7.4) for a day followed by subjecting to gel filtration using Sephadex G 150 gel column chromatography (Eluant: 0.1 M Tris-HCl buffer solution pH 7.4). Optical densities ($OD_{280}$ and $OD_{403}$) of each fraction obtained were measured and the fractions of which the peaks of $OD_{280}$ and $OD_{403}$ overlapped each other were collected.

(iii) Preparation of Agarose Gel

Agarose (a product of Iwai Kagaku Co., Ltd.) was suspended in 0.01 M Tris-HCl buffer solution (pH 7.5) in an amount of 1% by weight and the suspension was heated at 70° to 80° C. to dissolve. To this solution was added 0.01 v/v % of thimerosal and the resulting solution was poured into test tubes in an amount of 1 ml/tube followed by allowing to stand at room temperature to prepare 1 w/w % aqueous gel.

EXAMPLE 2-1

Polyethylene Glycol Method (i) Preparation of Test Sample

Five ml of blood was taken from each of twenty five patients with cancer, 2 patients with diseases other than cancer and 23 healthy persons using a syringe treated with heparin (500 units) and was centrifuged at 2,000 rpm for 10 minutes. The resulting supernatant (plasma) was used as test sample.

(ii) Determination

The test sample prepared in (i) above was placed in two test tubes in an amount of 200 µl/tube to which 50 µl each of the peroxidase labeled lectin preparation containing 3.5 µg/ml of lectin in Tris-HCl buffer solution (pH: about 7.5) prepared in Reference Step of Example 2 was added. After lightly stirring it the mixture was allowed to stand at 20° to 30° C. for 1 hour for reaction. Then, 250 µl of a solution of 8% (w/v) polyethylene glycol (molecular weight: 6,000) in 0.1 M Tris-HCl buffer solution was added to one of the test tubes and the mixture was stirred gently to form Sample A, and 250 µl of 0.1 M Tris-HCl buffer solution was added to another test tube and the mixture was stirred gently to form Sample B. Both Samples A and B were centrifuged for 40 to 60 minutes using a swing type rotor at 1,000 G after allowing the samples to stand at 20° to 30° C. for 30 to 60 minutes for reaction. Fifty µl of the resulting supernatant was collected and added to 2 ml of physiological salt solution prepared beforehand. After stirring it sufficiently the mixture was mixed with 500 µl of a substrate solution consisting of 0.1 M citrate buffer solution, orthophenylenediamine (fianl concentration 6% by weight) and 0.1% by weight of hydrogen peroxide and reacted at 20° to 30° C. for 30 minutes in the dark. The substrate solution was prepared beforehand and stored at 4° C., which is preferred. Thereafter, 1 ml of 2 N hydrochloric acid was added to the reaction mixture to stop the reaction and the color of the sample was measured spectrophotometrically in terms of optical density at 492 nm.

The amount of TAG-lectin complex being defined as difference (c) obtained by subtracting the optical density (a) of Sample A from the optical density (b) of Sample B was plotted in FIG. 1 in which the symbol O represents healthy persons and numerals (1) to (27) designate the following patients: (1) and (18) Gastric cancer; (2), (6), (9), (16) and (17) Lung cancer; (3), (5), (7), (8) and (13) Gastric cancer (early stage); (4) and (14) Progressive gastric cancer; (10) Heart failure; (11) Lymphadenitis; (12) Colon cancer which metastated to liver; (15) Uterine cancer metastated to lung; (19) Hydatidenmole; (20) Colon cancer; (21) Uterine cancer; (22) and (26) Ovarian cancer; (23) Rectal cancer; (24) Prostate cancer; (25) Urethral cancer; and (27) Hepatoma.

From the results shown in FIG. 1 it can be seen that samples showing (c) value higher than that observed in the samples from healthy persons contained TAG in amounts higher than the samples from healthy persons. From that it is strongly suggested that persons with high (c) value have tumor or cancer cells.

EXAMPLE 2-2

Gel Filtration Method (i) Blood was collected from 14 patients with cancer and 8 healthy persons and test samples were prepared therefrom in the same manner as Example 2.

(ii) Determination

Fifth μl of dilution of the test sample which had been prepared in (i) above and diluted $10^4$ fold with H solution which consisted of distilled water having dissolved therein 8% of sodium chloride, 0.4% of potassium chloride, 0.05% of sodium hydrogen phosphate, 0.06% of potassium dihydrogen phosphate, 0.05% of magnesium sulfate, 0.05% of magnesium chloride, 0.1% of calcium chloride, and 1% of glucose was mixed with 50 μl of the peroxidase labeled lectin preparation which had been prepared by Reference Step of Example 2, diluted 100 fold with 0.1 M phosphate buffer solution (pH 7.4) and incubated for 15 minutes in a water bath at 23° C. The resulting mixture was incubated for 15 minutes in a water bath at 23° C. and then imposed gently on the surface of agarose gel prepared by the method of Reference Step of Example 2. After incubating the test tube containing the gel in a water bath at 23° C. for 1 hour 2 ml of 0.1 M phosphate buffer solution (pH about 7.4) was added to the agarose gel which was then stirred. The supernatant was transferred immediately to a clean test tube to which was then added 400 μl of the substrate solution for peroxidase prepared in Reference Step of Example 2. After stirring it sufficiently the mixture was allowed to stand at room temperature for 15 minutes for reaction. The enzymatic reaction was stopped with 1 ml of 1 N hydrochloric acid the reaction mixture was stirred sufficiently using a thermomixer or like means. The optical density of the mixture thus treated was measured using a spectrophotometer at 492 nm. A mixture of 400 ml of the substrate solution and 1 ml of 1 N hydrochloric acid was used as a blank. The optical density values obtained were treated in the same manner as in Example 2-1 and the amount of TAG-lectin calculated was plotted in FIG. 2 in which symbol O represents healthy persons and numerals (1) to (10) indicates the following patients: (1) Gastric cancer; (2) Hydatidenmole; (3) Colon cancer; (4) Uterine cancer; (5) Ovarian cancer; (6) Rectal cancer; (7) Prostate cancer; (8) Urrethral cancer; (9) Hepatoma; and (10) Mammary cancer.

Figure 2:
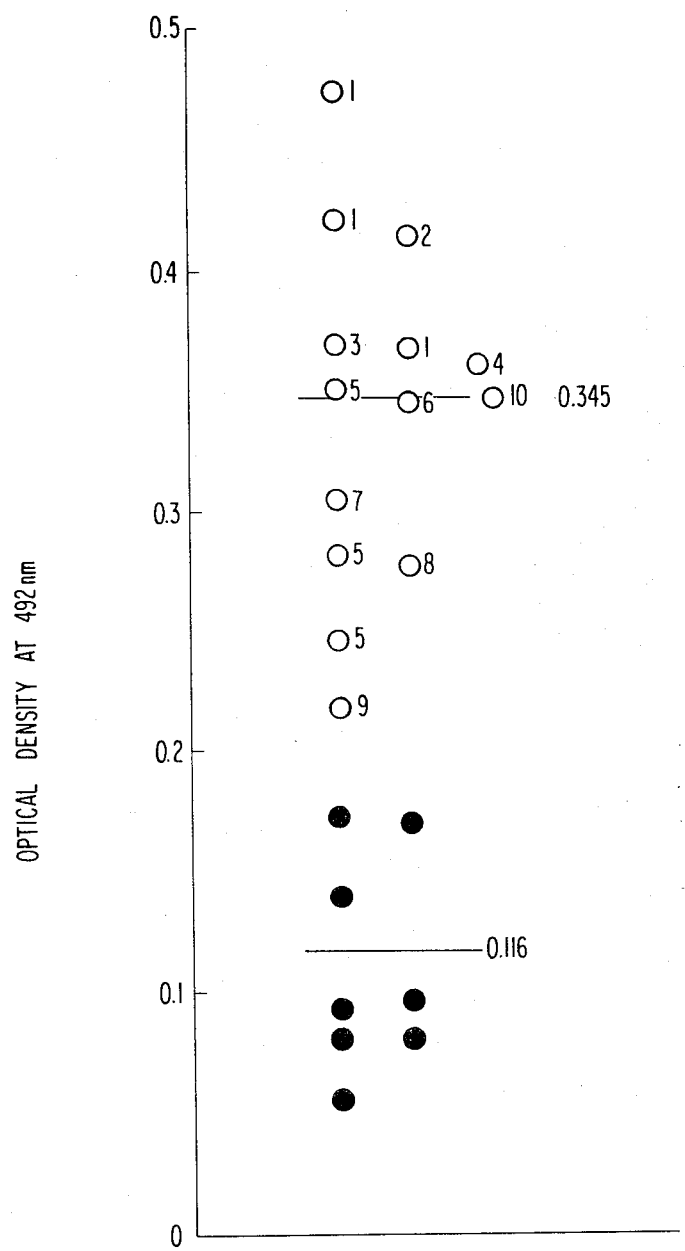
FIG. 2 is a graphical representation of the amounts of TAG determined according to Example 2 of this invention.

As will be evident from the results shown in FIG. 2 there is a remarkable difference in the level of TAG in body fluid between healthy persons and patients with various cancers.

This invention has practical applicability in clinical laboratories in the determination of TAG levels in body fluids, such as blood serum or plasma.

While the invention has been described in detail and with reference to specific embodiments thereof, it will be apparent to one skilled in the art that various changes and modifications can be made therein without departing from the spirit and scope thereof.

I claim:

1. A method for determining the level of tumor associated glycolinkage containing substance in a sample of body fluid which comprises reacting the tumor associated glycolinkage containing substance in a sample of the body fluid with a lectin capable of specifically combining with a terminal galactose ($\beta1\rightarrow$ or $\beta1\rightarrow4$)-N-acetylglucosamine or -N-acetylgalactosamine group to form a tumor associated glycolinkage-containing substance lectin complex and measuring the amount of the tumor associated glycolinkage-containing substance lectin complex or unreacted lectin.

2. The method of claim 1 which further comprises separating tumor associated glycolinkage containing substance from said body fluid sample and reacting the separate tumor associated glycolinkage containing substance with said lectin.

3. The method of claim 1 wherein a labeled lectin is used.

4. The method of claim 3 wherein said labeled lectin is a lectin labeled with an enzyme, a fluorescent substance or a radioactive substance.

5. The method of claim 3 wherein a protective protein is added to said body fluid.

6. The method of claim 1 wherein said body fluid is blood, tissue fluid, lymph, hydrothorax, ascites, amniotic fluid, gastric juice, urine, pancreatic juice, cerebrospinal fluid or saliva.

7. The method of claim 6 wherein said body fluid is blood serum or blood plasma.

8. The method of claim 1 wherein the reaction is carried out at 45° C. or less for at least 30 minutes.

9. The method of claim 8 wherein the reaction is carried out at 4° to 40° C.

10. The method of claim 8 wherein the reaction is carried out at 20° to 40° C.

11. The method of claim 8 wherein the reaction is carried out for 60 to 90 minutes.

12. The method of claim 1 wherein said lectin is a lectin which can specifically bind with galactose-($\beta1\rightarrow3$ or $\beta1\rightarrow4$)-N-acetylglucosamine and/or -N-acetylgalactose linkage(s).

13. The method of claim 12 wherein said lectin is peanut lectin or castor bean lectin.

14. The method of claim 2 wherein the amount of said unreacted lectin is determined by agglutination of said unreacted lectin.

15. The method of claim 14 wherein the unreacted lectin is agglutinated with a galactose-($\beta1\rightarrow3$ or $\beta1\rightarrow4$)-N-acetylglucosamine and/or -N-acetylgalactosamine terminal(s) containing glycoprotein or sephadex or glass beads coated therewith.

16. The method of claim 15 wherein said glycoprotein is rabbit erythrocyte or neuraminidase treated sheep erythrocyte.

17. The method of claim 4 wherein said enzyme is glucoamylase, glucose oxidase, peroxidase, alkaline phosphotase or hemeoctapeptide or active fragment thereof.

18. The method of claim 4 wherein said fluorescent substance is fluorescein, fluorescein hydrogen thiocyanate or dansyl chloride.

19. The method of claim 4 wherein said radioactive substance is radioactive iodine or tritium.

20. The method of claim 17 wherein said enzyme is peroxidase.

21. A method for the diagnosis of a cancer comprising determining the level of tumor associated glycolinkage containing substance in a sample of body fluid according to the method of claim 1 and comparing the tumor associated glycolinkage containing substance level obtained with that observed in healthy persons.

22. A kit for determining tumor associated glycolinkage containing substance level in a body fluid comprising lectin as a specific agglutinating agent for tumor associated glycolinkage containing substance.

23. The kit of claim 22 wherein said lectin has been lyophylized and the kit additionally contains a reconstituting reagent containing an aqueous based or water-miscible solvent.

24. The kit of claim 22 wherein said lectin is peanut lectin.

25. The method of claim 1, which comprises separating tumor associated glycolinkage containing substance from the body fluid, reacting the fluid with labelled or unlabelled lectin, separating the unreacted lectin from the reaction mixture and measuring the amount of unreacted lectin or tumor associated glycolinkage containing substance reacted lectin.

26. The method of claim 1, which comprises reacting a body fluid with labelled or unlabelled lectin, separating the reacted lectin from the unreacted lectin on a gel and measuring the amount of reacted or unreacted lectin.

* * * * *